US010077220B2

(12) United States Patent
Molinier et al.

(10) Patent No.: US 10,077,220 B2
(45) Date of Patent: *Sep. 18, 2018

(54) AROMATICS PRODUCTION PROCESS (71) Applicant: ExxonMobil Chemical Patents Inc., Baytown, TX (US)

(72) Inventors: Michel Molinier, Houston, TX (US); Kevin J. Knob, Fairfield, CA (US); Dennis J. Stanley, Houston, TX (US); Terri S. Vander Pol, Baytown, TX (US); Chunshe J. Cao, Conroe, TX (US); Xiaobo Zheng, Houston, TX (US); Thierry LeFlour, Paris (FR); Jacques Rault, Paris (FR); Stephane Claudel, Verneuil sur Seine (FR); Isabelle Prevost, Rueil Malmaison (FR); Jerome Pigourier, Meudon (FR); Celia Fernandez, Paris (FR)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/613,573

(22) Filed: Jun. 5, 2017

(65) Prior Publication Data

US 2017/0275218 A1    Sep. 28, 2017

Related U.S. Application Data (62) Division of application No. 14/743,048, filed on Jun. 18, 2015, now Pat. No. 9,708,233.

(Continued)

(51) Int. Cl.
*C07C 6/12* (2006.01)
*C07C 5/22* (2006.01)
(Continued)

(52) U.S. Cl.
CPC ............ *C07C 5/2732* (2013.01); *C07C 6/126* (2013.01); *C07C 7/005* (2013.01); *C07C 7/04* (2013.01)

(58) Field of Classification Search
CPC ................ C07C 6/12; C07C 5/22; C07C 4/24
(Continued)

(56) References Cited

U.S. PATENT DOCUMENTS 5,516,956 A     5/1996 Abichandani et al.
7,371,912 B2 *  5/2008 Schultz ................. C07C 5/2702
                                                    585/477
(Continued)

FOREIGN PATENT DOCUMENTS

CN    103664489 A    3/2014
CN    103880584 A    6/2014
(Continued)

OTHER PUBLICATIONS

Schultz et al., "Reduce Costs with Dividing-Wall Columns", CEP Magazine, May 2002, pp. 64-71.

*Primary Examiner* — Thuan D Dang
(74) *Attorney, Agent, or Firm* — Priya C. Prasad (57) ABSTRACT In a process for producing para-xylene, at least one feed comprising $C_{6+}$ aromatic hydrocarbons is supplied to a dividing wall distillation column to separate the feed into a $C_{7-}$ aromatic hydrocarbon-containing stream, a $C_8$ aromatic hydrocarbon-containing stream and a $C_{9+}$ aromatic hydrocarbon-containing stream. At least part of the $C_8$ aromatic hydrocarbon-containing stream is then supplied to a para-xylene recovery unit to recover para-xylene from the $C_8$ aromatic hydrocarbon-containing stream and produce a para-xylene depleted stream. The para-xylene depleted stream is contacted with a xylene isomerization catalyst in a xylene isomerization zone under conditions effective to isomerize xylenes in the para-xylene depleted stream and produce an isomerized stream, which is then at least partially recycled to the para-xylene recovery unit.

10 Claims, 7 Drawing Sheets

Related U.S. Application Data

(60) Provisional application No. 62/037,645, filed on Aug. 15, 2014.

(51) Int. Cl.
  *C07C 4/24* (2006.01)
  *C07C 5/27* (2006.01)
  *C07C 7/04* (2006.01)
  *C07C 7/00* (2006.01)

(58) Field of Classification Search
  USPC .................................. 585/478, 483, 470, 319
  See application file for complete search history.

(56) References Cited

U.S. PATENT DOCUMENTS

| 7,626,064 B1 | 12/2009 | Boldingh et al. |
| 7,663,010 B2 | 2/2010 | Levin |
| 2010/0152508 A1 | 6/2010 | Ou et al. |
| 2014/0155667 A1 | 6/2014 | Ou et al. |

FOREIGN PATENT DOCUMENTS

| WO | 2006/138063 A | 12/2006 |
| WO | 2012/145233 A | 10/2012 |
| WO | 2014/058465 A | 4/2014 |

* cited by examiner

AROMATICS PRODUCTION PROCESS

CROSS REFERENCE TO RELATED APPLICATIONS

This application is a divisional of Ser. No. 14/743,048, filed on Jun. 18, 2015 which claims priority to and the benefit of U.S. Provisional Application No. 62/037,645, filed Aug. 15, 2014, wherein the disclosures of each are incorporated herein by reference in their entireties.

FIELD OF THE INVENTION

This invention relates to a process for the production of aromatic hydrocarbons and particularly for the production of para-xylene.

BACKGROUND OF THE INVENTION

Benzene, toluene and xylenes (BTX) are important aromatic hydrocarbons, for which the worldwide demand is steadily increasing. The demand for xylenes, particularly para-xylene, has increased in proportion to the increase in demand for polyester fibers and film and typically grows at a rate of 5-7% per year. Benzene is a highly valuable product for use as a chemical raw material. Toluene is also a valuable petrochemical for use as a solvent and an intermediate in chemical manufacturing processes and as a high octane gasoline component. However, in many modern aromatic complexes, some or all of the benzene and/or toluene is converted to further xylenes by either transalkylation or methylation or a combination thereof.

A major source of benzene, toluene, and xylenes (BTX) is catalytic reformate, which is produced by contacting petroleum naphtha with a hydrogenation/dehydrogenation catalyst on a support. The resulting reformate is a complex mixture of paraffins and the desired $C_6$ to $C_8$ aromatics, in addition to a significant quantity of heavier aromatic hydrocarbons. After removing the light ($C_{5-}$) paraffinic components, the remainder of reformate is normally separated into $C_{7-}$, $C_8$ and $C_{9+}$-containing fractions using a plurality of distillation steps. Benzene can then be recovered from the $C_{7-}$-containing fraction to leave a toluene-rich fraction which is generally used to produce additional $C_8$ aromatics by either methylation or transalkylation with part of the $C_{9+}$-containing fraction. The $C_8$-containing fraction is fed to a xylene production loop where para-xylene is recovered, generally by adsorption or crystallization, and the resultant para-xylene depleted stream is subjected to catalytic conversion to isomerize the xylenes back towards equilibrium distribution and to reduce the level of ethylbenzene that would otherwise build up in the xylene production loop.

While catalytic technologies are becoming more efficient in achieving the desired chemical reactions to maximize para-xylene production while reducing loss of valuable aromatic molecules, there is a continuing need to achieve savings in hardware cost and energy consumption so as to reduce the overall para-xylene production cost.

SUMMARY OF THE INVENTION

According to the present invention, it has now been found that dividing wall distillation columns provide effective and energy-efficient means for separating hydrocarbon streams, particularly the $C_{7-}$, $C_8$, and $C_{9+}$-containing fractions, encountered in certain para-xylene production complexes.

In a first embodiment, at least one feed comprising $C_{6+}$ aromatic hydrocarbons is supplied to a dividing wall distillation column to separate the feed into a $C_{7-}$ aromatic hydrocarbon-containing stream, a $C_8$ aromatic hydrocarbon-containing stream and a $C_{9+}$ aromatic hydrocarbon-containing stream. At least part of the $C_8$ aromatic hydrocarbon-containing stream is then supplied to a para-xylene recovery unit to recover para-xylene from the $C_8$ aromatic hydrocarbon-containing stream and produce a para-xylene depleted stream, which is contacted with a xylene isomerization catalyst in a xylene isomerization zone under conditions effective to isomerize xylenes in the para-xylene depleted stream and produce an isomerized stream. At least part of the isomerized stream is then recycled to the para-xylene recovery unit.

In another embodiment, the process further comprises removing at least part of the aliphatic hydrocarbons from the $C_{7-}$ hydrocarbon-containing stream to produce a $C_{7-}$ aromatic hydrocarbon-enriched stream, which is supplied to a separation unit to separate the $C_{7-}$ aromatic-enriched stream into a benzene-containing stream and a toluene-containing stream. At least part of the toluene-containing stream and at least part of the $C_{9+}$ hydrocarbon-containing stream is contacted with a transalkylation catalyst under conditions effective to produce a transalkylation product containing xylenes, which are supplied to the para-xylene recovery unit.

Desirably, the process further comprises supplying at least part of the $C_8$ aromatic hydrocarbon-containing stream from (a1 or a2 or a3) to an ethylbenzene removal unit which is located upstream of the para-xylene recovery unit and which is operated under conditions effective to remove at least part of the ethylbenzene in the $C_8$ aromatic hydrocarbon-containing stream. Desirably, the conditions in the ethylbenzene removal unit are effective to maintain the $C_8$ aromatic hydrocarbon-containing stream substantially in the gas phase and the conditions in the xylene isomerization zone are effective to maintain the para-xylene depleted stream substantially in the liquid phase.

In a third embodiment, a feed comprising a mixture of $C_{6+}$ aliphatic and aromatic hydrocarbons is provided to a distillation column to separate the feed into a $C_{7-}$ hydrocarbon-containing stream and a $C_{8+}$ hydrocarbon-containing stream. At least part of the aliphatic hydrocarbons from the $C_{7-}$ hydrocarbon-containing stream are removed to produce a $C_{7-}$ aromatic hydrocarbon-enriched stream, which is supplied to a separation unit to recover benzene therefrom and produce a toluene-containing stream. At least part of the $C_{8+}$ hydrocarbon-containing stream is contacted with an ethylbenzene dealkylation catalyst under conditions effective to dealkylate ethylbenzene in the $C_{8+}$ hydrocarbon-containing stream and produce a dealkylation effluent comprising benzene and $C_{8+}$ hydrocarbons, which is separated in a dividing wall distillation column into a $C_{7-}$ aromatic hydrocarbon-containing stream, a $C_8$ aromatic hydrocarbon-containing stream and a $C_{9+}$ aromatic hydrocarbon-containing stream. The $C_8$ aromatic hydrocarbon-containing stream is then sent to a para-xylene recovery unit to recover para-xylene from the $C_8$ aromatic hydrocarbon-containing stream and produce a para-xylene depleted stream that is contacted with a xylene isomerization catalyst under conditions effective to isomerize xylenes in the para-xylene depleted stream and produce an isomerized stream, which is recycled to the dividing wall distillation column. At least part of the toluene-containing stream and at least part of the $C_{9+}$ hydrocarbon-containing stream is contacted with a transalkylation catalyst under conditions effective to produce a transalkylation product containing xylenes that is to the separation unit.

DETAILED DESCRIPTION OF THE EMBODIMENTS

The production of para-xylene from catalytic reformate requires a large number of costly fractionation steps. To reduce the capital and operating costs, the present invention employs one or more dividing wall distillation columns to separate various $C_{6+}$ hydrocarbon fractions into at least a $C_{7-}$ aromatic hydrocarbon-containing stream, a $C_8$ aromatic hydrocarbon-containing stream and a $C_{9+}$ aromatic hydrocarbon-containing stream. Benzene can then be recovered from the $C_{7-}$ aromatic hydrocarbon-containing stream, while the toluene can be used to produce additional xylenes by transalkylation with at least part of the $C_{9+}$ aromatic hydrocarbon-containing stream. The $C_8$ aromatic hydrocarbon-containing stream and additional xylenes produced by transalkylation are then fed to a para-xylene production loop comprising a para-xylene recovery unit and a xylene isomerization unit. At least part of the ethylbenzene contained in the reformate feed may be removed by dealkylation to benzene or by isomerization to xylenes, either upstream or downstream of the para-xylene recovery unit.

As its name implies, the term "dividing wall distillation column" refers to a particular known form of distillation column which comprises a dividing wall. The dividing wall vertically bisects a portion of the interior of the distillation column but does not extend to the top or bottom sections of the column, thus, enabling the column to be refluxed and reboiled similar to a conventional column. The dividing wall provides a fluid impermeable baffle separating the interior of the column. The inlet to the column is located on one side of the dividing wall while one or more side draws are located on the opposing side. The dividing wall enables the side of the column that does not have the inlet to function in a more stable manner with minimal effect from fluctuations in inlet flow rates, conditions or composition. This increased stability enables the column to be designed and operated in a manner that allows one or more side draw streams to be removed from the column having different compositions from either the overhead stream or the bottoms stream.

The ability to make three or more product streams from a single column can enable component separation with fewer distillation columns and possibly reduced capital and operating costs. The dividing wall distillation column can be used as a sole distillation column or multiple dividing wall distillation column can be used, either in series or parallel arrangements. The dividing wall distillation column can also be used in conjunction with one or more conventional distillation columns. Embodiments of the present invention can be particularly applicable when the optimum feed location to the column is above the optimum side draw location. If the feed location is above the side draw location in a conventional distillation column, the downward flow of the liquid feed within the column has a significant effect on the side draw composition. Variations in the feed flow rate, conditions or composition of the feed stream alter the side draw composition and make the production of a stable side draw stream very difficult to achieve.

In some embodiments, as shown in FIGS. 1, 2, 3, and 5, a dividing wall distillation column is employed in place of a conventional reformate splitter to fractionate the $C_{6+}$ hydrocarbon stream remaining after removal of the $C_{5-}$ aliphatic hydrocarbons from a catalytic reformate stream.

Figure 4:
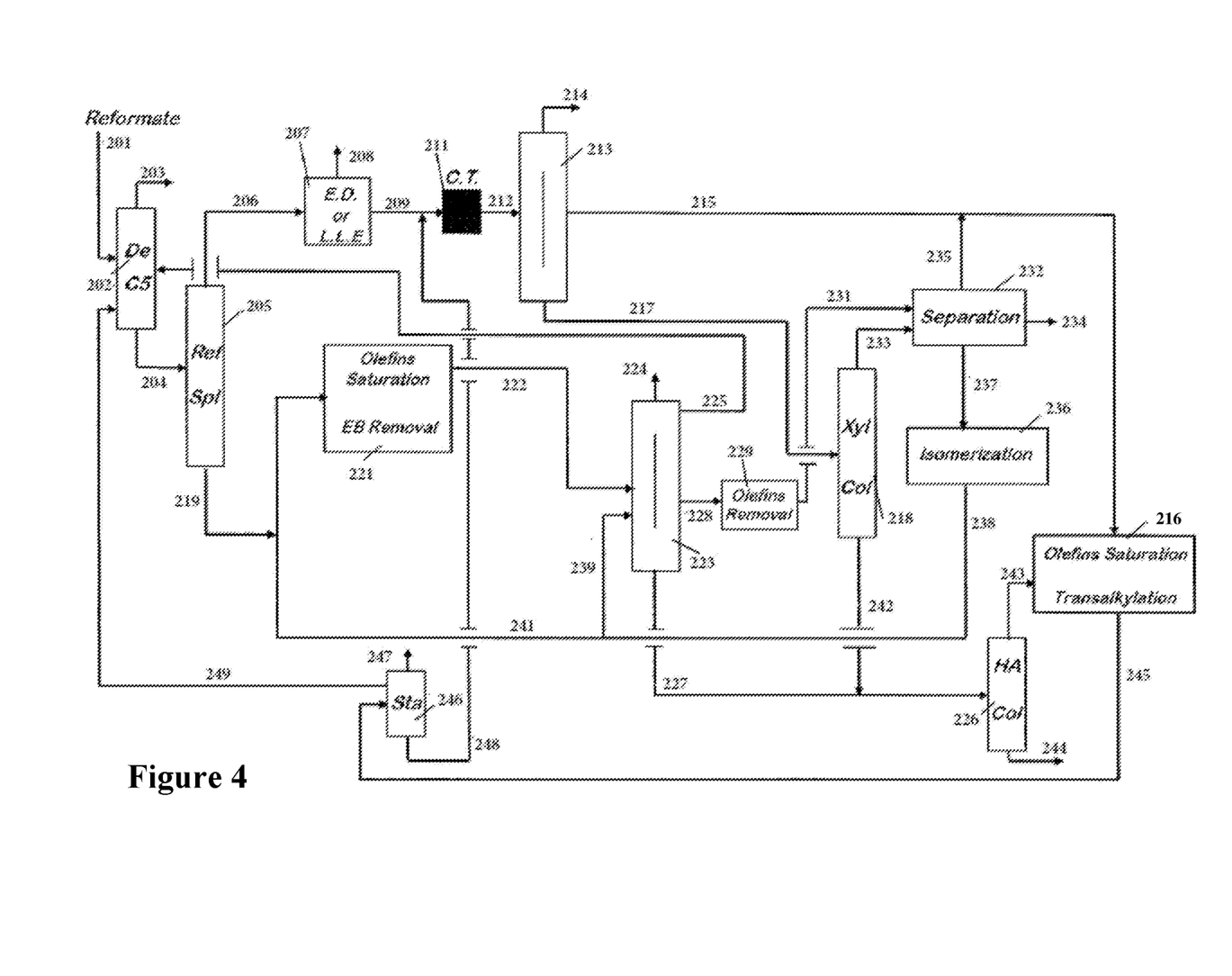
FIG. 4 is a flow diagram of a process for producing para-xylene from catalytic reformate according to a third embodiment of the invention.

In some embodiments, as shown in FIG. 4, the feed to the dividing wall distillation column is made up partly of the $C_{6+}$ aromatic hydrocarbon stream produced when ethylbenzene is removed by dealkylation from the $C_{8+}$ aromatic fraction from a conventional reformate splitter and partly of the effluent from the xylene isomerization unit.

It will therefore be seen that the dividing wall distillation column provides a cost-effective separation system for a variety of the feed and product streams encountered in a modern para-xylene production complex.

The invention will now be more particularly described with reference to the accompanying drawings.

Figure 1:
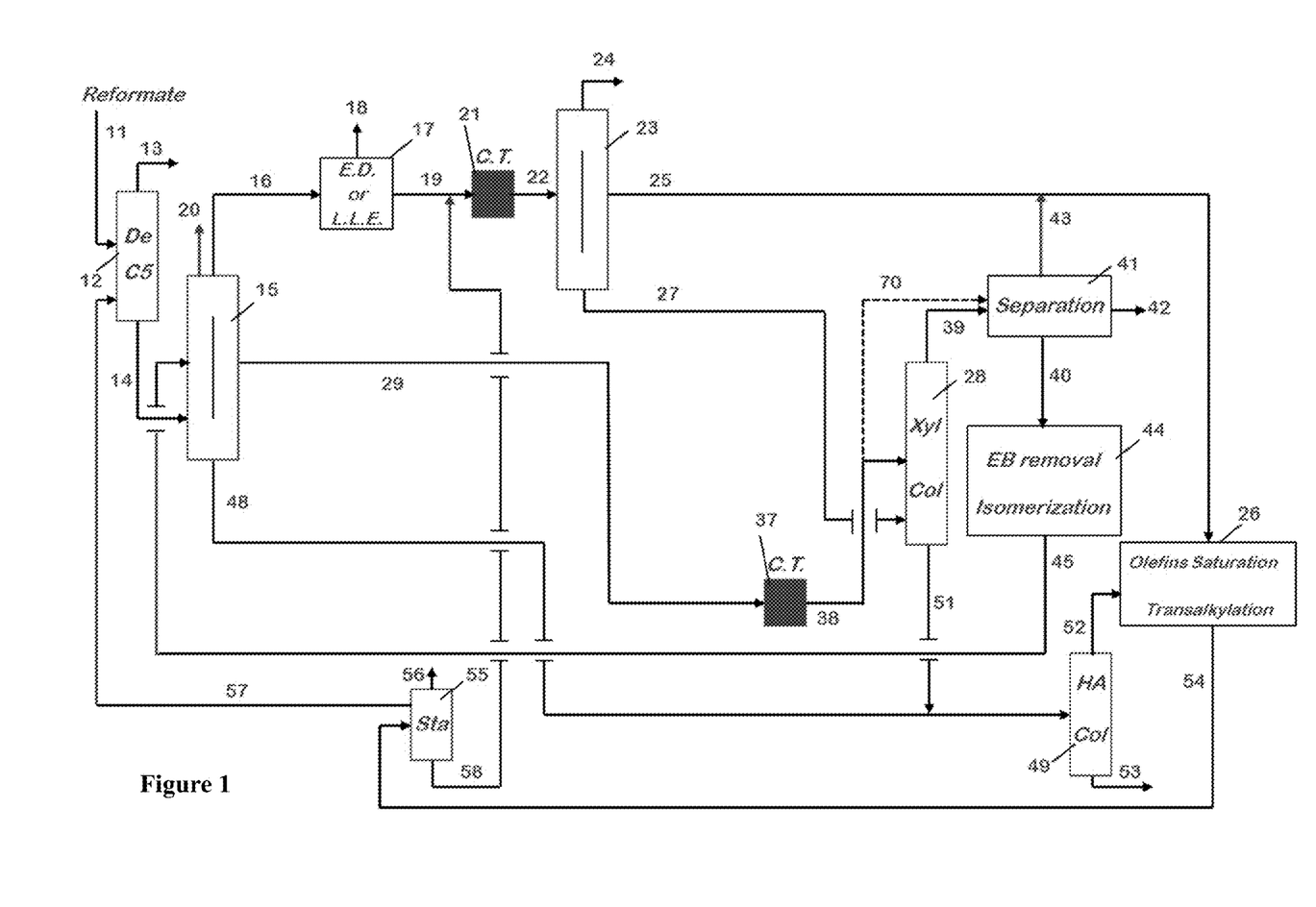
FIG. 1 is a flow diagram of a process for producing para-xylene from catalytic reformate according to a first embodiment of the invention.

FIG. 1 illustrates a process for producing para-xylene according to a first embodiment of the invention, in which a catalytic reformate feed stream containing aromatics is supplied by line 11 to a depentanizer section 12 to remove the $C_{5-}$ fraction. Pentane and lighter hydrocarbons are removed via line 13, while the $C_{6+}$ bottoms fraction is fed via line 14 to a dividing wall distillation column 15 to separate the bottoms fraction into $C_{7-}$, $C_8$, and $C_{9+}$ aromatic hydrocarbon-containing streams. Fuel gas separated in dividing wall distillation column 15 is collected via line 20.

The $C_{7-}$ containing stream from the dividing wall distillation column 15 is sent via line 16 to an extractive distillation or liquid-liquid extraction unit 17, where aliphatic hydrocarbons are removed via line 18 to leave a benzene- and toluene-enriched stream, which is fed via line 19 to an olefins saturation zone 21. The olefins saturation zone 21 may be a clay treater or any other means effective to remove olefins contaminants in aromatic streams, including catalytic processes, with optional hydrogen addition. The effluent from the olefins saturation zone 21 is fed via line 22 to a further dividing wall distillation column 23 from which benzene is collected via line 24, toluene is fed via line 25 to a transalkylation unit 26 and a $C_{8+}$ fraction is fed via line 27 to a xylenes distillation column 28.

The $C_8$ aromatic hydrocarbon-containing stream recovered from the reformate dividing wall column 15 is supplied by line 29 to an olefins saturation zone 37. The olefins saturation zone 37 may be a clay treater or any other means effective to remove olefins contaminants in aromatic streams, including catalytic processes, with optional hydrogen addition. The effluent from the olefins saturation zone 37 is fed via line 38 to the xylenes distillation column 28. Preferably, the effluent from the olefins saturation zone 37 is supplied to the column 28 separately from and above the supply point for the $C_{8+}$ fraction in line 27 since the stream in line 38 is much lighter than the stream in line 27.

The xylenes distillation column 28 separates an overhead $C_{9+}$-depleted stream from the feed to the distillation column 28. This overhead stream is then supplied via line 39 to a para-xylene separation section 41, where para-xylene is conventionally separated by adsorption or crystallization or a combination of both and recovered via line 42. Residual toluene in the overhead stream is removed from the para-xylene separation section 41 and fed to the transalkylation section 26 via line 43, while the remaining para-xylene-depleted stream is fed to an ethylbenzene removal and xylene isomerization section 44 via line 40. When paraxylene is separated by adsorption, the adsorbent used preferably contains a zeolite. Typical adsorbents used include crystalline alumino-silicate zeolites either natural or synthetic, such as for example zeolite X or Y or mixtures thereof. These zeolites are preferably exchanged by cations such as alkali or alkaline earth or rare earth cations. The adsorption column is preferably a simulated moving bed column (SMB) and a desorbant is used such as for example, paradiethylbenzene, paradifluorobenzene, diethylbenzene or toluene or mixtures thereof.

In the ethylbenzene removal and xylene isomerization section 44, ethylbenzene removal is preferably achieved in the gas phase and carried out either by dealkylation to benzene or by isomerization to xylenes. Where the preferred mechanism is dealkylation to benzene, any conventional catalytic process for the dealkylation of ethylbenzene can be used. However, in one preferred embodiment, the dealkylation is effected in the presence of a catalyst comprising an intermediate pore size zeolite (that is having a Constraint Index of 1 to 12 as defined in U.S. Pat. No. 4,016,218) and a hydrogenation component, optionally in combination with a non-acidic binder, such as silica. Examples of suitable intermediate pore size zeolites include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-21 (U.S. Pat. No. 4,046,859); ZSM-22 (U.S. Pat. No. 4,556,477); ZSM-23 (U.S. Pat. No. 4,076,842); ZSM-35 (U.S. Pat. No. 4,016,245); ZSM-38 (U.S. Pat. No. 4,406,859); ZSM-48 (U.S. Pat. No. 4,397,827); ZSM-57 (U.S. Pat. No. 4,046,685); and ZSM-58 (U.S. Pat. No. 4,417,780). Examples of suitable hydrogenation components include the oxide, hydroxide, sulfide, or free metal (i.e., zero valent) forms of Group 8-10 metals (i.e., Pt, Pd, Ir, Rh, Os, Ru, Ni, Co, and Fe), Group 14 metals (i.e., Sn and Pb), Group 15 metals (i.e., Sb and Bi), and Group 7 metals (i.e., Mn, Tc, and Re). Noble metals (i.e., Pt, Pd, Ir, and Rh) or Re are preferred hydrogenation components. Combinations of catalytic forms of such noble or non-noble metal, such as combinations of Pt with Sn, may be used. As used herein, the numbering scheme for the groups of the Periodic Table of the Elements is as disclosed in Chemical and Engineering News, 63(5), 27 (1985).

In one preferred embodiment, the dealkylation catalyst is selectivated, either before introduction into the dealkylation reactor or in-situ in the reactor, by contacting the catalyst with a selectivating agent, such as at least one organosilicon in a liquid carrier and subsequently calcining the selectivated catalyst at a temperature of 350 to 550° C. The selectivation procedure alters the diffusion characteristics of the catalyst such that the catalyst requires at least 50 minutes to sorb 30% of its equilibrium capacity of ortho-xylene at 120° C. and at an ortho-xylene partial pressure of 4.5±0.8 mm of mercury. One example of a selectivated ethylbenzene dealkylation catalyst is described in U.S. Pat. No. 5,516,956, the entire contents of which are incorporated herein by reference.

Suitable conditions for the gas phase dealkylation of ethylbenzene using the above-described catalyst include a temperature from about 400° F. to about 1000° F. (204 to 538° C.), a pressure from about 0 to about 1,000 psig (100 to 7000 kPa), a weight hourly space velocity (WHSV) of between about 0.1 and about 200 $hr^{-1}$, and a hydrogen to hydrocarbon molar ratio from about 0.5 to about 10. Preferably, these conversion conditions include a temperature of from about 660° F. to about 900° F. (350° C. to 480° C.), a pressure from about 50 to about 400 psig (446 to 2860 kPa), a WHSV of between about 3 and about 50 $hr^{-1}$ and a hydrogen to hydrocarbon molar ratio from about 0.7 to about 5. The WHSV is based on the weight of catalyst composition, i.e., the total weight of active catalyst and, if used, binder therefor. The conversion conditions are selected so that the $C_8$ aromatic hydrocarbon-containing feed is substantially in the gas phase in the ethylbenzene removal section 44.

In the ethylbenzene removal and xylene isomerization section 44, xylene isomerization is also preferably achieved in the gas phase. Any gas phase catalytic isomerization process known to those skilled in the art can be used to effect the xylene isomerization in section 44, but one preferred catalytic system employs an intermediate pore size zeolite having different ortho-xylene diffusional properties than the ethylbenzene removal catalyst. Thus, in one embodiment, the xylene isomerization catalyst requires less than 50 minutes to sorb 30% of the equilibrium capacity of ortho-xylene at 120° C. and at an ortho-xylene partial pressure of 4.5±0.8 mm of mercury.

The xylene isomerization conditions employed in the ethylbenzene removal and xylene isomerization section 44 are selected so as to isomerize xylenes in the para-xylene depleted stream, and thereby produce an isomerized stream having a higher concentration of para-xylene than the para-xylene depleted stream. Suitable conditions include a temperature of from about 660° F. and about 900° F. (350° C. to 480° C.), a pressure from about 50 to about 400 psig (446 to 2860 kPa), a WHSV of between about 3 and about 50 $hr^{-1}$ and a hydrogen to hydrocarbon molar ratio from about 0.7 to about 5. The WHSV is based on the weight of catalyst composition, i.e., the total weight of active catalyst and, if used, binder therefor.

One preferred process for operating the ethylbenzene removal and xylene isomerization section 44 is described in U.S. Pat. No. 5,516,956.

The effluent from the ethylbenzene removal and xylene isomerization section 44 is supplied via line 45 to the dividing wall distillation column 15 to separate said effluent into $C_{7-}$, $C_8$ and $C_{9+}$ aromatic hydrocarbon-containing streams.

The $C_{9+}$ aromatic hydrocarbon-containing stream recovered from the reformate dividing wall distillation column 15 is supplied via line 48 to a heavy aromatics distillation column 49, which also receives the bottoms stream from the xylenes distillation column 28 via line 51. The heavy aromatics distillation column 49 separates the $C_{9+}$ aromatic hydrocarbons supplied by lines 48 and 51 into a $C_9/C_{10}$/light $C_{11}$-containing fraction which is removed in line 52 and $C_{11}+$-containing fraction which is supplied to the gasoline pool, a fuel oil pool, or to a topping column via line 53. The $C_9/C_{10}$/light $C_{11}$-containing fraction 52 is then fed to the transalkylation unit 26 in combination with the toluene-enriched streams supplied via lines 25 and 43, optionally after passage through an olefins saturation zone, such as clay treating or any other means to remove olefins contaminants including catalytic processes, with optional hydrogen addition. In FIG. 1, the olefins saturation zone is shown combined with the transalkylation zone in a single unit 26, but the purpose of this schematic representation is not to be limiting. Those skilled in the art know that olefins saturation can be carried out in a unit located upstream of and separated from the transalkylation unit. Furthermore, olefins saturation is carried out only when required, and thus, if for instance stream 52 requires olefins removal while olefins content in stream 25 is such that no olefins removal is required, then only stream 52 will pass through the olefins saturation zone.

Any transalkylation process known to those skilled in the art can be used, but one preferred process employs the multi-stage catalytic system described in U.S. Pat. No. 7,663,010, incorporated herein by reference in its entirety. Such a system comprises (i) a first catalyst comprising a first molecular sieve having a Constraint Index in the range of 3-12 and containing 0.01 to 5 wt % of at least one source of a first metal element of Groups 6-10 of the Periodic Table and (ii). a second catalyst comprising a second molecular sieve having a Constraint Index less than 3 and comprising 0 to 5 wt % of at least one source of a second metal element of Groups 6-10 of the Periodic Table, wherein the weight ratio of the first catalyst or the second catalyst is in the range of 5:95 to 75:25 and wherein the first catalyst is located upstream of the second catalyst.

Examples of suitable molecular sieves having a Constraint Index of 3-12 for use in the first catalyst include ZSM-5, ZSM-11, ZSM-22, ZSM-23, ZSM-35, ZSM-48, ZSM-57, and ZSM-58, with ZSM-5 being preferred. Examples of suitable molecular sieves having a Constraint Index of less than 3 for use in the second catalyst include zeolite beta, zeolite Y, Ultrastable Y (USY), Dealuminized Y (Deal Y), mordenite, ZSM-3, ZSM-4, ZSM-12, ZSM-18, NU-87, and ZSM-20, with ZSM-12 being preferred. Specific examples of useful metals for each of the first and second catalysts include iron, ruthenium, osmium, nickel, cobalt, rhenium, molybdenum, tin, and noble metals such as platinum, rhodium, iridium or palladium.

The transalkylation process can be conducted in any appropriate reactor including a radial flow, fixed bed, continuous down flow or fluid bed reactor. The conditions in the first and second catalyst bed can be the same or different but generally comprise a temperature from 100 to 1000° C., preferably in the range of 300 to 500° C.; a pressure in the range of 790 to 7000 kPa-a (kilo-Pascal absolute), preferably in the range of 2170 to 3000 kPa-a, a hydrogen to hydrocarbon molar ratio from 0.01 to 20, preferably from 1 to 10; and a WHSV from 0.01 to 100 $hr^{-1}$, preferably in the range of 1-20 $hr^{-1}$.

The effluent from the transalkylation unit 26 is fed via line 54 to a stabilizer 55, where light gas is collected and removed via line 56. A side stream from the stabilizer 55 is recycled to the depentanizer 12 via line 57 and the stabilizer bottoms are fed to the benzene/toluene/C8+ dividing wall column 23 via line 58, optionally via olefin saturation zone 21.

Compared to a state-of-the-art aromatics complex using conventional distillation units in place of the dividing wall column section 15, one advantage of the embodiment shown in FIG. 1 is to enable to removal of a large portion of the $C_{9+}$ content of the reformate $C_8$ cut feeding the xylene loop. To a lesser extent, the same advantage also applies to the isomerate $C_8$ cut, which also has a reduced $C_{9+}$ fraction (if any) will also be removed. Since both the $C_8$ aromatics fractions from the reformer section and from the isomerization section are $C_{9+}$ depleted, they can be sent to the xylenes column 28 at a feed tray located above the feed tray receiving the $C_8$ aromatics fraction originating from the transalkylation unit. This is illustrated in FIG. 1 by stream in line 38 being located above the stream in line 27. In addition, if $C_{9+}$ species content in the stream in line 38 is within the specification of the separation section 41, then a portion or all of this stream can bypass the xylene column 28 and be directly fed to separation section 41, as shown by the dotted line 70. Depending on the severity of the fractionation achieved in dividing wall column section 15 and the tolerance of the separation section 41 for $C_{9+}$ compounds, either option above or a combination of both can be considered. These options will reduce the overall energy consumption of the xylene column 28 as compared with that of a state-of-the-art aromatics complex without a dividing wall column.

In a modification (not shown) of the process shown in FIG. 1, the ethylbenzene removal and xylene isomerization section 44 is divided into two separate reactors, both located downstream of the para-xylene separation section 41. The two reactors can be arranged in parallel or in series, in the latter case with the ethylbenzene removal reactor normally being located upstream of the xylene isomerization reactor. In this modification, the ethylbenzene removal reactor can be operated under significantly different conditions than the xylene isomerization reactor. For example, the ethylbenzene removal reactor can be operated substantially in the gas phase, while the xylene isomerization reactor may be operated substantially in the liquid phase to reduce xylenes losses during the isomerization process.

Figure 2:
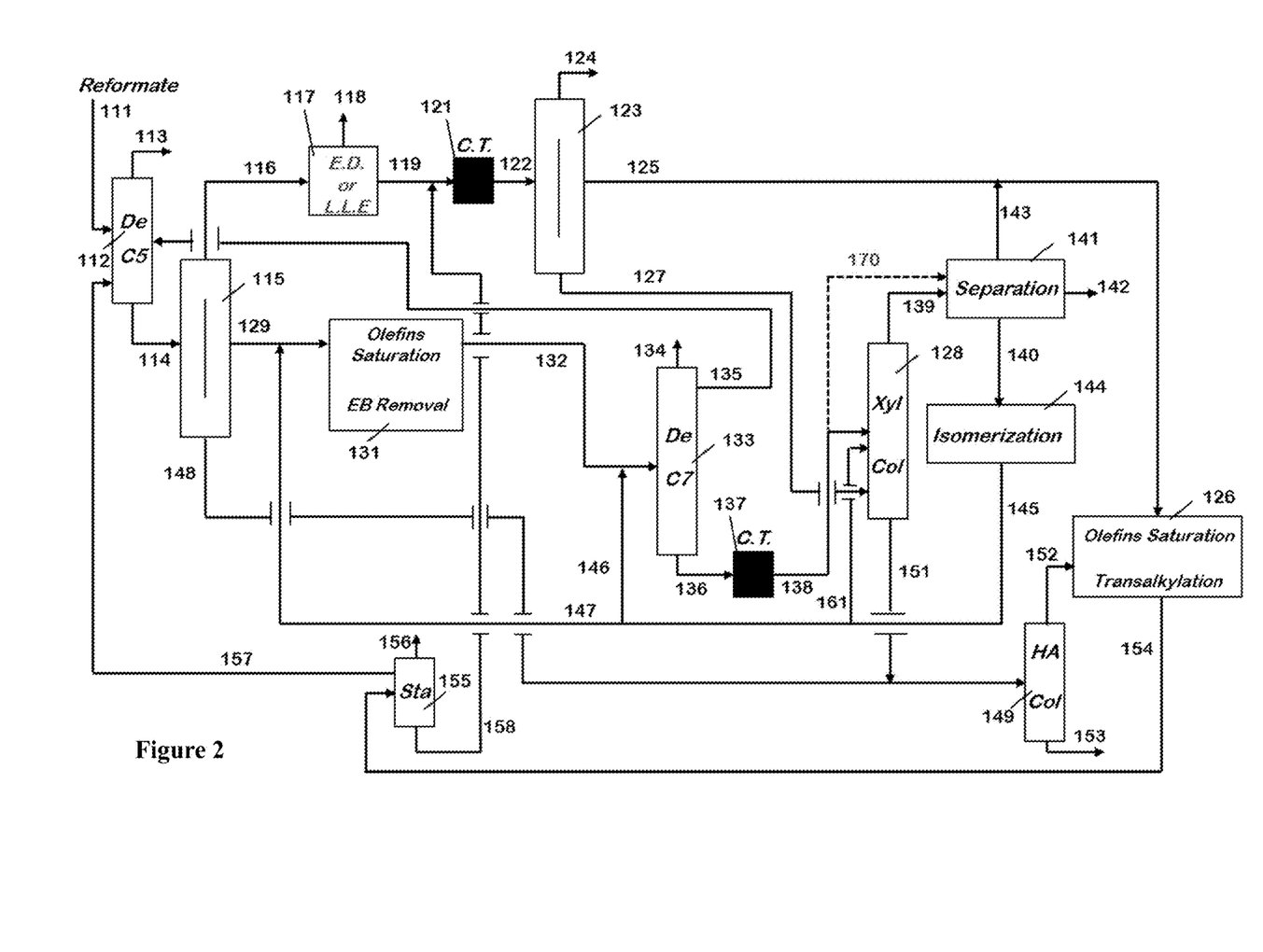
FIG. 2 is a flow diagram of a process for producing para-xylene from catalytic reformate according to a second embodiment of the invention.

FIG. 2 illustrates a process for producing para-xylene according to a second embodiment of the invention, in which a dividing wall distillation column is again employed in place of a conventional reformate splitter to fractionate the $C_{6+}$ hydrocarbon stream remaining after removal of the $C_{5-}$ aliphatic hydrocarbons from a catalytic reformate stream. Thus in the second embodiment, a catalytic reformate feed stream containing aromatics is supplied by line 111 to a depentanizer section 112 to remove the $C_{5-}$ fraction. Pentane and lighter hydrocarbons are removed via line 113, while the $C_{6+}$ bottoms fraction is fed via line 114 to a dividing wall distillation column 115 to separate the bottoms fraction into $C_{7-}$, $C_8$ and $C_{9+}$ aromatic hydrocarbon-containing streams.

The $C_{7-}$ stream is sent via line 116 to an extractive distillation or liquid-liquid extraction unit 117, where aliphatic hydrocarbons are removed via line 118 to leave a benzene- and toluene-enriched stream, which is fed via line 119 to an olefins saturation zone 121. The olefins saturation zone 121 may be a clay treater or any other means effective to remove olefins contaminants in aromatic streams, including catalytic processes, with optional hydrogen addition. The effluent from the olefins saturation zone 121 effluent is fed via line 122 to a further dividing wall distillation column 123 from which benzene is collected via line 124, toluene is fed via line 125 to a transalkylation unit 126 and the $C_{8+}$ fraction is fed via line 127 to a xylenes distillation column 128, preferably towards the bottom of said xylenes distillation column 128.

Unlike the embodiment shown in FIG. 1, in the second embodiment shown in FIG. 2 the $C_8$ aromatic hydrocarbon-containing stream recovered from the reformate dividing wall column 115 is supplied by line 129 to an ethylbenzene removal reaction section 131, which is located upstream of the xylenes distillation column 128 and separately from the xylene isomerization section. Optionally, the $C_8$ aromatic hydrocarbon-containing stream in line 129 can be supplied to the ethylbenzene removal reaction section 131 by way of an olefins saturation zone, such as clay treating or any other means to remove olefins contaminants including catalytic processes, with optional hydrogen addition.

As in the FIG. 1 embodiment, ethylbenzene removal can be carried out in gas phase or liquid phase, but is preferably achieved in gas phase, and carried out either by dealkylation to benzene or by isomerization to xylenes. Where the preferred mechanism is dealkylation to benzene, suitable and preferred catalysts and conditions for the dealkylation are described about with reference to the FIG. 1 embodiment.

The effluent from the ethylbenzene removal section 131 is supplied via line 132 to a deheptanizer 133, from which fuel gas is removed via line 134, a $C_6/C_7$ stream is redirected to the depentanizer section 112 via line 135, and a xylenes-enriched effluent is fed via line 136 to an olefins saturation zone 137, typically a clay treater or any other means to remove olefins contaminants including catalytic processes, with optional hydrogen addition. The effluent from the olefins saturation zone 137 is fed via line 138 to the xylenes distillation column 128, preferably separately from and above the heavier $C_{8+}$ fraction in line 127.

The overhead of the xylenes distillation column 128 is supplied via line 139 to a para-xylene separation section 141, where para-xylene is conventionally separated by adsorption or crystallization or a combination of both and recovered via line 142. Residual toluene is removed from the para-xylene separation section 141 and fed to the transalkylation section 126 via line 143, while the remaining para-xylene-depleted stream is fed to a xylene isomerization section 144 via line 140. The para-xylene separation section 141 is substantially similar to the para-xylene separation section 41 described above.

The xylene isomerization section 144 can be operating in the gas phase or the liquid phase, but is preferably operated in the liquid phase. Any liquid phase catalytic isomerization process known to those skilled in the art can be used in the xylene isomerization section 144, but one preferred catalytic system is described in U.S. Patent Application Publication Nos. 2011/0263918 and 2011/0319688, the entire contents of each of which are incorporated herein by reference.

The conditions in the xylene isomerization section 144 are selected so as to isomerize xylenes in the para-xylene depleted stream, while maintaining the para-xylene depleted stream substantially in the liquid phase, and thereby produce an isomerized stream having a higher concentration of para-xylene than the para-xylene depleted stream. Suitable conditions include a temperature from about 230° C. to about 300° C., a pressure from about 1300 to about 2100 kPa and a weight hourly space velocity (WHSV) of from about 0.5 to about 10 $hr^{-1}$.

The effluent from the xylene isomerization section 144 is supplied via line 145 to a split between recycle to the xylene column 128 via line 161, recycle to the deheptanizer 133 via line 146, or rerouting to the ethylbenzene removal reaction section 131 via line 147. Rerouting of the xylene isomerization section effluent in line 145 between line 161, line 146 and line 147 can be optimized depending on the ethylbenzene content and overall composition of said effluent.

The $C_{9+}$ aromatic hydrocarbon-containing stream recovered from the reformate dividing wall distillation column 115 is supplied via line 148 to a heavy aromatics distillation column 149, which also receives the bottoms stream from the xylenes distillation column 128 via line 151. The heavy aromatics distillation column 149 separates the $C_{9+}$ aromatic hydrocarbons supplied by lines 148 and 151 into a $C_9/C_{10}$/light $C_{11}$-containing fraction which is removed in line 152 and $C_{11}$+-containing fraction which is supplied to the gasoline pool, a fuel oil pool, or to a topping column via line 153.

The $C_9/C_{10}$/light $C_{11}$-containing fraction 152 is then fed to the transalkylation unit 126 in combination with the toluene-enriched streams supplied via lines 125 and 143, optionally after passage through an olefins saturation zone, such as clay treating or any other means to remove olefins contaminants including catalytic processes, with optional hydrogen addition. In FIG. 2, the olefins saturation zone is shown combined with the transalkylation zone in a single unit 126, but the purpose of this schematic representation is not to be limiting. Those skilled in the art know that olefins saturation can be carried out in a unit located upstream of and separated from the transalkylation unit. Furthermore, olefins saturation is carried out only when required, and thus if for instance stream 152 requires olefins removal while olefins content in stream 125 is such that no olefins removal is required, then only stream 152 will pass through the olefins saturation zone. A suitable transalkylation process is described above with reference to the FIG. 1 embodiment.

Any transalkylation process known to those skilled in the art can be used, but one preferred process employs the multi-stage catalytic system described in U.S. Pat. No. 7,663,010, incorporated herein by reference in its entirety. Such a system comprises (i) a first catalyst comprising a first molecular sieve having a Constraint Index in the range of 3-12 and containing 0.01 to 5 wt % of at least one source of a first metal element of Groups 6-10 of the Periodic Table and (ii) a second catalyst comprising a second molecular sieve having a Constraint Index less than 3 and comprising 0 to 5 wt % of at least one source of a second metal element of Groups 6-10 of the Periodic Table, wherein the weight ratio of the first catalyst or the second catalyst is in the range of 5:95 to 75:25 and wherein the first catalyst is located upstream of the second catalyst.

Examples of suitable molecular sieves having a Constraint Index of 3-12 for use in the first catalyst include ZSM-5, ZSM-11, ZSM-22, ZSM-23, ZSM-35, ZSM-48, ZSM-57, and ZSM-58, with ZSM-5 being preferred. Examples of suitable molecular sieves having a Constraint Index of less than 3 for use in the second catalyst include zeolite beta, zeolite Y, Ultrastable Y (USY), Dealuminized Y (Deal Y), mordenite, ZSM-3, ZSM-4, ZSM-12, ZSM-18, NU-87, and ZSM-20, with ZSM-12 being preferred. Specific examples of useful metals for each of the first and second catalysts include iron, ruthenium, osmium, nickel, cobalt, rhenium, molybdenum, tin, and noble metals such as platinum, rhodium, iridium or palladium.

The transalkylation process can be conducted in any appropriate reactor including a radial flow, fixed bed, continuous down flow or fluid bed reactor. The conditions in the first and second catalyst bed can be the same or different but generally comprise a temperature from 100 to 1000° C., preferably in the range of 300 to 500° C.; a pressure in the range of 790 to 7000 kPa-a (kilo-Pascal absolute), preferably in the range of 2170 to 3000 kPa-a, a hydrogen to hydrocarbon molar ratio from 0.01 to 20, preferably from 1 to 10; and a WHSV from 0.01 to 100 $hr^{-1}$, preferably in the range of 1-20 $hr^{-1}$.

The effluent from the transalkylation unit 126 is fed via line 154 to a stabilizer 155, where light gas is collected and removed via line 156. A side stream from the stabilizer 155 is recycled to the depentanizer 112 via line 157 and the stabilizer bottoms are fed to the benzene/toluene/C8+ dividing wall column 123 via line 158, optionally via olefin saturation zone 121.

As in the FIG. 1 embodiment, if the $C_{9+}$ species content in the stream in line 138 is within the specification of the separation section 141, then a portion or all of this stream can bypass the xylene column 128 and be directly fed to separation section 141, as shown by the dotted line 170.

Figure 3:
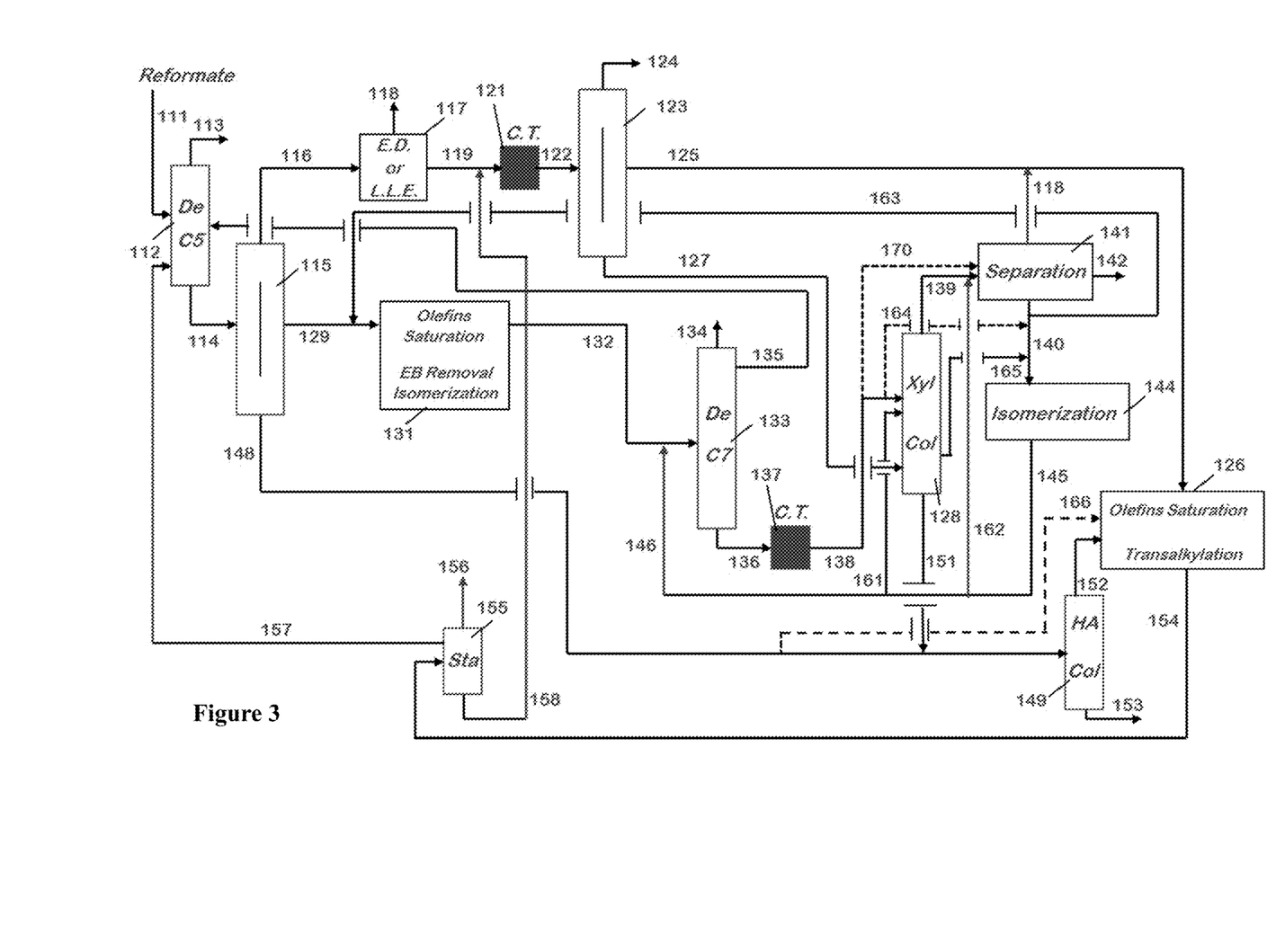
FIG. 3 is a flow diagram illustrating processes for producing para-xylene from catalytic reformate according to modifications of the second embodiment of the invention.

FIG. 3 illustrates various possible modifications of the process shown in FIG. 2 and employs like reference numerals to indicate like components. In one such modification, the isomerized $C_8$ aromatics recycle stream 147 to the section 131 (see FIG. 2) is replaced by a para-xylene depleted $C_8$ aromatics recycle stream 163 (see FIG. 3), which is taken upstream of the isomerization unit 144 while recycle stream 147 was taken downstream of the isomerization unit 144. When the catalyst used in the ethylbenzene removal section 131 is selectivated as discussed above, xylene losses tend to increase with para-xylene concentration in the feed because the molecular sizes of ethylbenzene and para-xylene are similar. Hence while ortho and meta-xylene diffusion into the catalyst pores is restricted, para-xylene—just like ethylbenzene—will easily react on catalytic active sites, thereby increasing xylene losses. However, because the effluent from separation section 141 is para-xylene depleted, its addition via line 163 to the feed to the ethylbenzene removal section 131 will dilute the para-xylene content in the feed and hence xylene losses through the ethylbenzene removal section 131 will be reduced.

Another modification, shown in FIG. 3, of the second embodiment is to recirculate a portion of the effluent from the isomerization section 144 directly to the para-xylene separation section 141 via line 162. When the liquid phase isomerization section 144 operates at conditions that yield little to no benzene, or when this benzene yield does not impact the para-xylene separation section 141 performance, it may be advantageous, as already shown in FIG. 2, to recirculate a portion of the effluent from the isomerization section 144 directly to the xylenes column 128 via line 161. Furthermore, when the liquid phase isomerization section 144 operates at conditions that yield little to no benzene and little to no $C_9$+ aromatics, or when these yields do not impact the performance of the para-xylene separation section 141, it may be advantageous, as shown in FIG. 3, to recycle a portion of the effluent from the isomerization section 144 directly to the para-xylene separation section 141 via line 162. Benzene yield and $C_9$+ aromatic yield from liquid phase isomerization are usually related to the operating temperature of the unit and also to the ethylbenzene content of the unit feed. Thus, depending on the efficiency of the catalyst in the ethylbenzene removal section 131 and on the state of the catalyst in the liquid phase isomerization unit 144 (a liquid phase isomerization catalyst will typically operate at lower temperature early in the cycle and at higher temperature late in the cycle), as well as on the type of adsorbent and desorbent used in the para-xylene separation section 141, distribution of the liquid phase isomerization effluent through lines 146, 161 and 162 can be optimized. Such recycles 162 and 161 can also be implemented in other process schemes envisaged herein.

In a further modification shown in FIG. 3, the gas phase ethylbenzene removal reaction section 131, optionally fed by way of an olefins saturation zone, such as clay treating or any other means to remove olefins contaminants including catalytic processes, with optional hydrogen addition, is replaced by a gas phase ethylbenzene removal and xylenes isomerization section. Therefore, in addition to ethylbenzene removal either by ethylbenzene dealkylation to benzene or by ethylbenzene isomerization to xylenes, xylenes isomerization will also take place in section 131. One example of a suitable combined ethylbenzene removal/xylene isomerization system is disclosed in U.S. Pat. No. 5,516,956, referred to above. By conducting some xylene isomerization in section 131, the effluent of section 131 supplied via line 132 to the deheptanizer 133 and then further to the separation section 141 via lines 136, 138, and 139 has higher para-xylene concentration than in the scheme described in FIG. 2. This means the para-xylene to xylenes ratio is higher than in the scheme described in FIG. 2, and thus a smaller separation unit 141 will be needed. It should be noted that the concept of adding a xylenes isomerization function to ethylbenzene removal section is also applicable to other process schemes envisaged herein.

Another modification, shown in FIG. 3, of the process shown in FIG. 2 is the addition of optional bypass 164 from stream 138 to the liquid phase isomerization section 144. When stream 138 contains little or no para-xylene, it is advantageous to isomerize the xylenes in the stream 138 prior to circulating the xylenes to the xylene column 128 via line 161 and separation section 141 so as to reduce traffic in these sections and hence associated operating costs. This alternative is more particularly suited when isomerization efficiency in section 131 is low because little or no xylenes isomerization catalyst has been loaded in section 131 and hence the primary function of section 131 is ethylbenzene removal, and furthermore if stream 129 is heavily diluted with stream 163.

Another modification, shown in FIG. 3, of the process shown in FIG. 2 is the optional addition of stream 165 from the xylenes column 128 to the effluent line 140 from the separation section 141. When stream 165 is collected at an ortho-xylene rich location of the xylenes column 128, this recycle to the liquid phase isomerization section 144 allows for a stream with low para-xylene content to be isomerized to close to equilibrium xylenes without circulation through the separation section 141, hence reducing traffic through said separation section and associated operating costs. This modification is also applicable to other process schemes envisaged herein.

Another modification, shown in FIG. 3, of the process shown in FIG. 2 is the addition of optional bypass stream 166 from stream 148 to the olefins saturation and transalkylation section 126. When the $C_{11}$+ content of the stream 148 is low, which may occur when the end point of the reformate cut stream 111 is low, at least a portion of said stream 148 can bypass the heavy aromatics column 149 and be directed to olefins saturation and transalkylation section 126 via line 166, thereby reducing traffic through the heavy aromatics column 149 and associated operating costs. This modification is also applicable to the schemes presented in FIG. 1, FIG. 2 and FIG. 4. As previously mentioned, in FIG. 3, the olefins saturation zone is shown combined with the transalkylation zone in a single unit 126, but the purpose of this schematic representation is not to be limiting. Those skilled in the art know that olefins saturation can be carried out in a unit located upstream of and separated from the transalkylation unit. Furthermore, olefins saturation is carried out only when required, and thus if for instance streams 152 and 166 require olefins removal while olefins content in stream 125 is such that no olefins removal is required, then only streams 152 and 166 will pass through the olefins saturation zone.

Another optional modification of the scheme depicted in FIG. 3 is the separation of the isomerization recycle streams from the two isomerization sections, namely the gas phase isomerization section 131 and the liquid phase isomerization section 144. These recycle streams can then be supplied at different feed points (see line 138 feeding gas phase isomerization effluent to xylenes column 128 and line 161 feeding liquid phase isomerization effluent to xylenes column 128 on FIG. 3) of the xylenes column 128 according to their $C_9$ aromatics content, hence reducing the size and energy consumption of the column.

FIG. 4 illustrates a process for producing para-xylene according to a third embodiment of the invention, in which a conventional reformate splitter is employed to fractionate the $C_{6+}$ hydrocarbon stream remaining after removal of the $C_{5-}$ aliphatic hydrocarbons from a catalytic reformate stream. Thus, in the third embodiment, a reformate feed stream containing aromatics is supplied by line 201 to a depentanizer section 202 to remove the $C_{5-}$ fraction. Pentane and lighter hydrocarbons are removed via line 203, while the $C_{6+}$ bottoms fraction is fed via line 204 to a conventional reformate splitter 205 to separate the bottoms fraction into $C_{7-}$ and $C_{8+}$ aromatic hydrocarbon-containing streams.

The $C_{7-}$ stream from the reformate splitter 205 is sent via line 206 to an extractive distillation or liquid-liquid extraction unit 207, where aliphatic hydrocarbons are removed via line 208 to leave a benzene- and toluene-enriched stream, which is fed via line 209 to an olefins saturation zone 211. The olefins saturation zone 211 may be a clay treater or any other means effective to remove olefins contaminants in aromatic streams, including catalytic processes, with optional hydrogen addition. The effluent from the olefins saturation zone 211 is fed via line 212 to a dividing wall distillation column 213 from which benzene is collected via line 214, toluene is fed via line 215 to a transalkylation unit 216 and the $C_{8+}$ fraction is fed via line 217 to a xylenes distillation column 218.

The $C_{8+}$ aromatic hydrocarbon-containing stream recovered from the reformate splitter 205 is supplied by line 219 to an ethylbenzene removal section 221, optionally by way of an olefins saturation zone, such as clay treating or any other means to remove olefins contaminants including catalytic processes, with optional hydrogen addition. The ethylbenzene removal in section 221 is preferably carried out by deethylation to benzene and light ($C_2$) gas, preferably in the gas phase, as described above. Alternatively, ethylbenzene removal can also be carried out by isomerization to xylenes.

The effluent from the ethylbenzene removal section 221 is supplied via line 222 to a further dividing wall distillation column 223, from which fuel gas is removed via line 224, a $C_6/C_7$ stream is redirected to the depentanizer section 202 via line 225, a $C_{9+}$ stream is fed to a heavy aromatics column 226 via line 227, and a xylenes-enriched $C_8$ stream is fed via line 228 to an olefins saturation zone 229, typically any process to remove olefins contaminants including catalytic processes, with optional hydrogen addition. The effluent from the olefins saturation zone 229 is fed via line 231 to a para-xylene separation section 232, which also receives the overhead from the xylenes distillation column 218 via line 233. Para-xylene is conventionally separated by adsorption or crystallization or a combination of both in para-xylene separation section 232 and recovered via line 234. Residual toluene is removed from the para-xylene separation section 232 and fed to the transalkylation section 216 via line 235, while the remaining para-xylene-depleted stream is fed to a xylene isomerization section 236 via line 237.

Any xylene isomerization process known to those skilled in the art can be used in the xylene isomerization section 236, but one preferred process is conducted in the liquid phase and employs a catalytic system as described in U.S. Patent Application Publication Nos. 2011/0263918 and 2011/0319688, the entire contents of each of which are incorporated herein by reference.

The effluent from the xylene isomerization section 236 is supplied via line 238 to a split between recycle to the dividing wall distillation column 223 via line 239 or rerouting to the ethylbenzene removal section 221 via line 241. Where the ethylbenzene removal section 221 operates at very high conversion rate (about 50% or higher), the slip stream rerouted to the ethylbenzene removal section via line 241 will be very small and most of the isomerization section effluent will be redirected to the dividing wall distillation column 223 via line 239.

The $C_{9+}$ stream from the dividing wall distillation column 223 is supplied via line 227 to the heavy aromatics distillation column 226, which also receives the bottoms stream from the xylenes distillation column 218 via line 242. The heavy aromatics distillation column 226 separates the $C_{9+}$ aromatic hydrocarbons supplied by lines 227 and 242 into a $C_9/C_{10}$-containing fraction which is removed in line 243 and a $C_{11}$-containing fraction which is supplied to the gasoline pool via line 244. The $C_9/C_{10}$-containing fraction 243 is then fed to the transalkylation unit 216 together with the toluene-enriched stream supplied via line 215, optionally after passage through an olefins saturation zone, such as clay treating or any other means to remove olefins contaminants including catalytic processes, with optional hydrogen addition. In FIG. 4, the olefins saturation zone is shown combined with the transalkylation zone in a single unit 216, but the purpose of this schematic representation is not to be limiting. Those skilled in the art know that olefins saturation can be carried out in a unit located upstream of and separated from the transalkylation unit. Furthermore, olefins saturation is carried out only when required, and thus if for instance stream 243 requires olefins removal while olefins content in stream 215 is such that no olefins removal is required, then only stream 243 will pass through the olefins saturation zone.

Any transalkylation process known to those skilled in the art can be used in the transalkylation unit 216, but one preferred process employs the multi-stage catalytic system described in U.S. Pat. No. 7,663,010 as discussed above for the FIG. 1 embodiment.

The effluent from the transalkylation unit 216 is fed via line 245 to a stabilizer 246, where light gas is collected and removed via line 247. A side stream from the stabilizer 246 is recycled to the depentanizer 202 via line 249 and the stabilizer bottoms are fed to the dividing wall distillation column 213 via line 248, optionally via olefin saturation zone 211.

It will be seen that, in the second and third embodiments shown in FIGS. 2 to 4, ethylbenzene removal is carried out in sections 131, 221 on an EB-rich $C_8$ aromatics mixture recovered from the fractionation of a reformate effluent, whereas xylene isomerization is carried out in a dedicated section 144, 236 on a para-xylene depleted stream. This arrangement decouples ethylbenzene removal from xylenes isomerization, thereby enabling the isomerization of the large para-depleted xylenes stream to be effected in the liquid phase (without addition of a gas-phase isomerization unit), whereas the EB removal is performed on a smaller EB-rich stream in the gas phase. This reduces the costs associated with reboiling liquid effluent from the paraxylene separation section 141, 232, which is required for isomerization of the para-depleted xylenes in a gas phase isomerization unit, when both catalytic reactions are carried out in the same unit 44, as shown in FIG. 1. In addition, decoupling ethylbenzene removal from xylenes isomerization reduces catalyst costs since liquid phase isomerization catalysts are typically metal-free while gas phase isomerization catalysts include either precious metals or costly non-precious metals, such as rhenium. Further overall xylenes loop efficiency can be increased since the conditions for each process can be set independently so as to maximize its yield and efficiency throughout the plant useful life.

According to a fourth embodiment (exemplified in FIG. 7 described below), the schemes illustrated in FIGS. 1 to 3 can be modified by replacing the first dividing wall column 15, 115 by a conventional distillation column allowing the separation of three cuts: namely a $C_{7-}$ cut as the top cut, a $C_8$ cut as a side draw and a $C_{9+}$ cut as the bottom cut. When the $C_8$ cut is fed to the EB removal section 131 (FIG. 2 or 3) or 211 (FIG. 4), this solution leads to sending more $C_9$ in the $C_8$ cut to the ethylbenzene removal unit than in the case of a dividing wall column. Some of the $C_9$ components will be dealkylated to toluene and thus, the toluene/$C_{9+}$ ratio in the transalkylation feed will increase and the benzene/PX ratio in the aromatic complex will also increase, which can be of interest when more benzene production is targeted, provided that the catalytic system in the EB removal unit can process heavier feed without significant impact to EB removal efficiency of said EB removal unit. In this case, the $C_{9+}$ cut may contain some residual $C_8$ aromatics and should be either directed to heavy aromatics distillation column or to the xylene distillation column.

Figure 6:
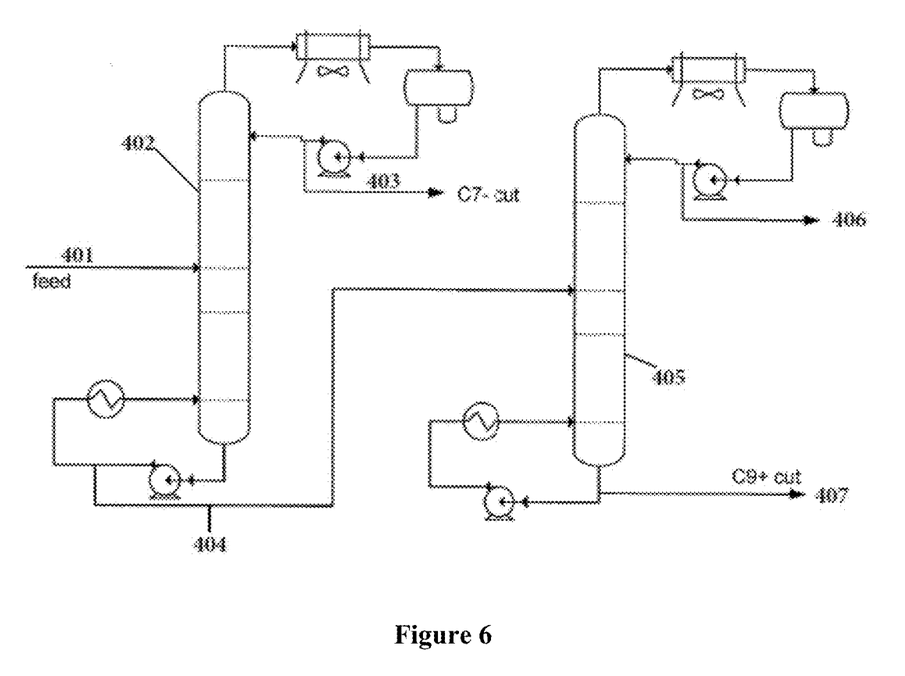
FIG. 6 depicts a conventional 2 columns fractionation system for the separation of the $C_{7-}/C_8/C_{9+}$ streams in an aromatics complex.

Some configuration options have not been described herein, but within the scope of the present disclosure, namely: (a) in the schemes depicted in the figures below, the dividing wall column 23 in FIG. 1, the dividing wall column 123 in FIGS. 2 & 3, and the dividing wall column 213 in FIG. 4 can be replaced by a conventional arrangement of benzene and toluene columns; (b) in the schemes depicted in the figures below, the dividing wall column 15 in FIG. 1 and the dividing wall column 115 in FIGS. 2 & 3 can be replaced by a conventional arrangement of light reformate splitter and heavy reformate splitter columns as depicted in FIG. 6; (c) in the schemes depicted in FIGS. 2 & 3 below, the EB removal unit 131 (FIG. 2) or the EB removal and xylenes isomerization unit 131 (FIG. 3) can optionally be located between the depentanizer 112 and the dividing wall column 115 on stream 114 instead of downstream of dividing wall column 115 on stream 129; and (d) similarly, in the scheme depicted in FIG. 4 below, the EB removal unit 221 can optionally be located between the depentanizer 202 and the reformate splitter 205 on stream 204 instead of downstream of reformate splitter 205 on stream 219.

The invention will now be more particularly described with reference to the following non-limiting Examples.

Example 1

This example illustrates the benefit of implementing a dividing wall column (FIG. 5) as compared with conventional light and heavy reformate splitters (FIG. 6) in the configuration schemes depicted in FIGS. 1 to 3.

This example is based on a 85 wt % rich $C_{6+}$ aromatic hydrocarbon stream, obtained from the reforming of a naphtha feed with the following carbon number distribution:

| | |
|---|---|
| C7- | 17% |
| C7 | 31% |
| C8 | 32% |
| C9+ | 20% |

Figure 5:
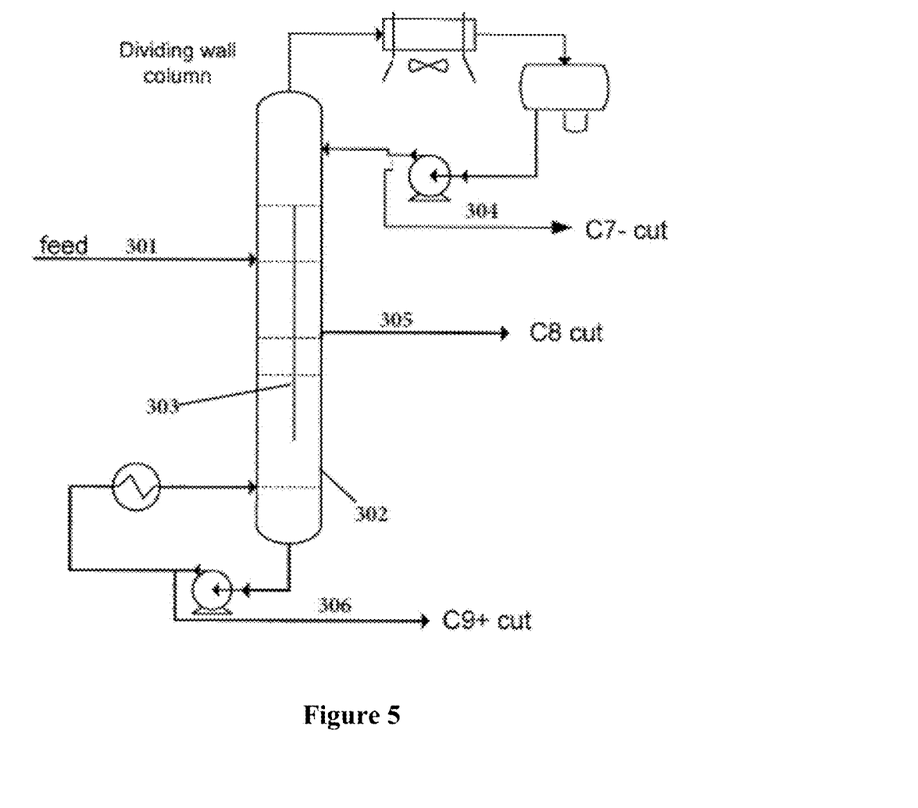
FIG. 5 depicts a dividing wall column fractionation system for the separation of the $C_{7-}/C_8/C_{9+}$ streams in an aromatics complex.

Referring to FIG. 5, 220 t/h of the rich $C_{6+}$ aromatic hydrocarbon feed (stream 301) is fed to a dividing wall column 302 which is operated at a pressure of 1.4 kPa, a condenser temperature is 83° C., and a reboiler temperature of 209° C. The dividing wall column (DWC) 302 contains 58 theoretical plates, including condenser (plate N° 1) and reboiler (plate N° 58). DWC technology involves placing a vertical partition between the feed or pre-fractionator, and product sides of a three product tower. The separation of low and high boiling fractions occurs in the feed side, and the separation of the medium boiling fraction occurs in the product side. The pre-fractionator side of the DWC distributes the middle key between the top and bottom, allowing great flexibility to match composition at top and bottom of the main column.

In the example shown in FIG. 5, a vertical wall 303 in the dividing wall column 302 extends from tray N° 11 down to tray N° 37 and allows each of these trays to be partitioned into 2 zones: a feed zone and a draw zone located on each side of the wall. The rich C6+ aromatic hydrocarbon feed stream 301 is introduced into the dividing wall column 302 at plate N° 13 on the feed zone side of the wall section. The dividing wall column 302 allows the production of a $C_{7-}$ cut (stream 304) as liquid distillate on plate N° 1, a $C_8$ cut (stream 305) as a side draw from plate N° 23 on the draw zone side of the wall 303, and a $C_{9+}$ cut (stream 306) as the bottom product. Condensing is performed using an air cooler removing 30 MW, reboiling is ensured by a heating medium providing 33.3 MW of heat at a minimum of 214° C., and preferably at 15° C. above the bottom temperature of the dividing wall column 302.

The fractionation performance of the dividing wall column 302 is summarized below:

Toluene recovery (defined as toluene in $C_{7-}$ cut (stream 304) divided by toluene in the feed (stream 301)) is 99.9 wt %.

$C_8$ aromatics recovery (defined as EB+PX+MX+OX in $C_8$ cut (stream 305) divided by EB+PX+MX+OX in the feed (stream 301)) is 99 wt %.

$C_9$ aromatics content in the C8 cut (stream 305) is 5 wt %.

In order to achieve the separation performance described above, conventional fractionation would require using 2 distillation columns implemented in series as shown in FIG. 6. Thus, referring to FIG. 6, 220 t/h of the rich $C_{6+}$ aromatic hydrocarbon feed (stream 401) is fed on plate N° 15 of a first distillation column 402. This first distillation column 402 contains 29 theoretical plates and is operated at a pressure of 1.4 kPa, a condenser temperature of 83° C. and a reboiler temperature of 175° C. Condensing is performed using an air cooler removing 26.7 MW, reboiling is ensured by a heating medium providing 29.6 MW of heat at a minimum of 180° C., and preferably at 15° C. above the bottom temperature of the first column. The first distillation column 402 allows the recovery of a $C_{7-}$ cut (stream 403) as liquid distillate on plate N° 1, and a $C_{8+}$ cut (stream 404) as bottom product.

The fractionation performance of the first distillation column 402 is summarized below:

Toluene recovery (defined as toluene in $C_{7-}$ cut (stream 403) divided by toluene in the feed (stream 401)) is 99.9 wt %.

$C_8$ aromatics recovery (defined as EB+PX+MX+OX in $C_{8+}$ cut (stream 404) divided by EB+PX+MX+OX in the feed (stream 401)) is 99.5 wt %.

The bottom product of the first distillation column 402 (stream 404) feeds a second distillation column 405, containing 29 theoretical plates, and operated at 1.4 kPa, a condenser temperature of 144° C. and a reboiler temperature is 197° C. Condensing is performed using an aircooler removing 13.7 MW, reboiling is ensured by a heating medium providing 19.5 MW of heat at a minimum of 202° C., and preferably at 15° C. above the bottom temperature of the second column. The second distillation column 405 allows the recovery of a $C_8$ cut (stream 406) as liquid distillate on plate N° 1, and a $C_{9+}$ cut (stream 407) as bottom product.

The fractionation performance of the second distillation column 405 is summarized below:

$C_8$ aromatics recovery (defined as EB+PX+MX+OX in $C_8$ cut (stream 406) divided by EB+PX+MX+OX in the feed (stream 404)) is 99.5 wt %.

$C_9$ aromatics content in the $C_8$ cut (stream 406) is 5 wt %.

Thus, the fractionation performance of the system consisting of the 2 fractionation columns in series (FIG. 6) is similar to the fractionation performance of the dividing wall column (FIG. 5). However, compared to the conventional arrangement shown in FIG. 6, the dividing wall column shown in FIG. 5 is more energy efficient since the heat requirement to perform the same fractionation performance has been reduced from 49.1 MW down to 33.3 MW. An additional advantage of the dividing wall column compared to conventional arrangement is to reduce by half the fractionation system hardware (number of columns, reboilers, etc.) required to obtain the desired fractionation performance.

Example 2

Figure 7:
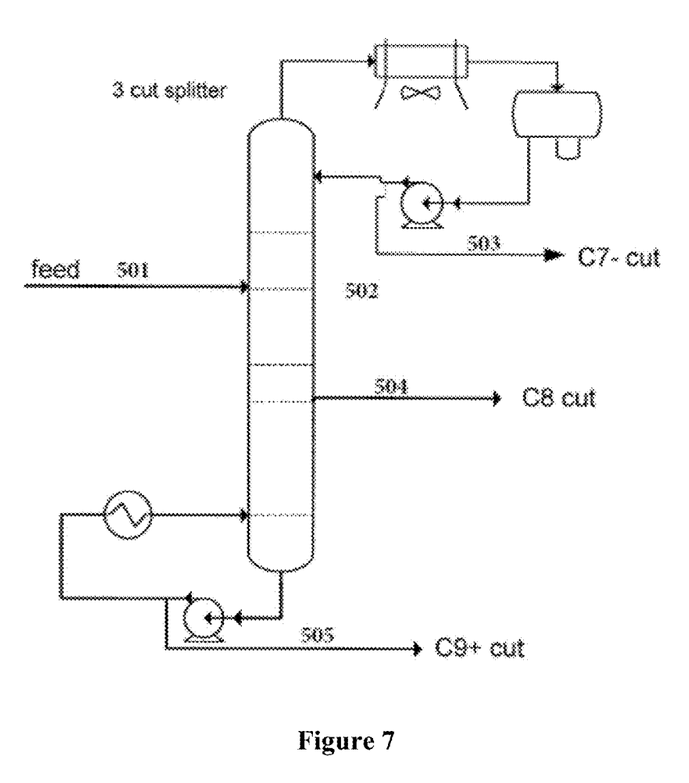
FIG. 7 depicts a 3-cut splitter fractionation system for the separation of the $C_{7-}/C_8/C_{9+}$ streams in an aromatics complex.

Referring now to FIG. 7, this example illustrates the effect of implementing a 3-cut distillation column instead of dividing wall column as the reformate splitter 15, 115 in the configuration schemes depicted in FIGS. 1 to 3.

In the embodiment of FIG. 7, 220 t/h of the rich C6+ aromatic hydrocarbon feed (stream 501) is fed on plate N° 20 of a 3-cut distillation column 502 containing 58 theoretical plates, and operated at 1.4 kPa, a condenser temperature of 83° C. and a reboiler temperature of 202° C. This 3-cut distillation column 502 produces a $C_{7-}$ cut (stream 503) as liquid distillate on plate N° 1, a $C_8$ cut (stream 504) as a side draw from plate N° 40, and a $C_{9+}$ cut (stream 505) as the bottom product. Condensing is performed using an air cooler removing 31 MW, reboiling is ensured by a heating medium providing 33.7 MW of heat at a minimum of 207° C., and preferably at 15° C. above the bottom temperature of the distillation column.

The fractionation performance of the 3-cut distillation column 502 is downgraded compared to what was achieved with the dividing wall column in Example 1 and is summarized below:

The toluene recovery (defined as toluene in $C_7$ cut (stream 503) divided by toluene in the feed (stream 501)) is 99.9 wt %.

$C_8$ aromatics recovery (defined as EB+PX+MX+OX in $C_8$ cut (stream 504) divided by EB+PX+MX+OX in the feed (stream 501)) is 87 wt %.

$C_9$ aromatics content in the $C_8$ cut (stream 504) is 15 wt %.

However the ethylbenzene recovery (defined as the EB in the $C_8$ cut divided by EB in the feed) achieved with the 3-cut distillation column (98 wt %) is similar to that obtained with the dividing wall column in Example 1 (98.5 wt %).

The performance of the distillation schemes of Example 1 and Example 2 are summarized in Table 1 below, in which Qr signifies the heat requirement.

|  |  | Conventional 2 Columns | DWC | Conventional 1 column with 3 cuts |
|---|---|---|---|---|
| Qr (MW) | Col 1 | 29.6 | 33.3 | 33.6 |
|  | Col 2 | 19.5 |  |  |
|  | Total | 49.1 |  |  |
| T (° C.) | Col 1 | 175.2 | 209.2 | 202 |
|  | Col 2 | 196.7 |  |  |
| Plate Number | Col 1 | 29 | 58 | 58 |
|  | Col 2 | 29 |  |  |
|  | Total | 58 |  |  |
| Diameter (m) | Col 1 | 4.7 | 5.2 | 4.9 |
|  | Col 2 | 4 |  |  |
| Performances | Toluene recovery in Light reformate | 99.90 wt % | 99.90 wt % | 99.90 wt % |
|  | C8A recovery in C8A cut | 99 wt % | 99 wt % | 87 wt % |
|  | C9A content in C8A cut | 5 wt % | 5 wt % | 15 wt % |

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group of consisting of," or "is" preceding the recitation of the composition, component, or components, and vice versa.

The invention claimed is:

1. A process for producing para-xylene and benzene, the process comprising:
    (a2) supplying a feed comprising a mixture of $C_{6+}$ aliphatic and aromatic hydrocarbons to a dividing wall distillation column to separate the feed into a $C_{7-}$ hydrocarbon-containing stream, a $C_8$ hydrocarbon-containing stream and a $C_{9+}$ hydrocarbon-containing stream;
    (b2) removing at least part of the aliphatic hydrocarbons from the $C_{7-}$ hydrocarbon-containing stream to produce a $C_{7-}$ aromatic hydrocarbon-enriched stream;
    (c2) supplying at least part of the $C_{7-}$ aromatic-enriched stream to a separation unit to separate the $C_{7-}$ aromatic-enriched stream into a benzene-containing stream and a toluene-containing stream;
    (d2) supplying at least part of the $C_8$ hydrocarbon-containing stream to a para-xylene recovery unit to recover para-xylene from the $C_8$ hydrocarbon-containing stream and produce a para-xylene depleted stream;
    (e2) contacting at least part of the para-xylene depleted stream with a xylene isomerization catalyst in a xylene isomerization zone under conditions effective to isomerize xylenes in the para-xylene depleted stream and produce an isomerized stream;
    (f2) recycling at least part of the isomerized stream to the para-xylene recovery unit;
    (g2) contacting at least part of the toluene-containing stream and at least part of the $C_{9+}$ hydrocarbon-containing stream with a transalkylation catalyst under conditions effective to produce a transalkylation product containing xylenes; and
    (h2) supplying at least part of the xylenes in the transalkylation product to the para-xylene recovery unit; wherein at least part of the transalkylation product from (g2) is supplied to the separation unit in (c2) and the separation unit is effective to separate xylenes from the transalkylation product and to separate the $C_{7-}$ aromatic-enriched stream into the benzene-containing stream and the toluene-containing stream, and wherein the separation unit in (c2) comprises a further dividing wall distillation column.

2. The process of claim 1, wherein the feed to (a2) is produced by removing $C_{5-}$ hydrocarbons from a reformate stream.

3. The process of claim 1 and further comprising:
    (i2) supplying at least part of the $C_8$ aromatic hydrocarbon-containing stream from (a2) to an ethylbenzene removal zone which is located upstream of the para-xylene recovery unit; and
    (j2) contacting the $C_8$ aromatic hydrocarbon-containing stream with a first catalyst in the ethylbenzene removal zone under conditions effective to remove at least part of the ethylbenzene in the $C_8$ aromatic hydrocarbon-containing stream prior to (d2).

4. The process of claim 3, wherein the ethylbenzene removal zone also contains a second catalyst effective under said conditions to isomerize xylenes in the $C_8$ aromatic hydrocarbon-containing stream.

5. The process of claim 3, wherein the conditions in the ethylbenzene removal zone are effective to maintain the $C_8$ aromatic hydrocarbon-containing stream substantially in the gas phase.

6. The process of claim 5, wherein the conditions in the xylene isomerization zone are effective to maintain the para-xylene depleted stream substantially in the liquid phase.

7. The process of claim 1 and further comprising:
    (k2) supplying at least part of the para-xylene depleted stream from (d2) to an ethylbenzene removal zone which is located upstream of the xylene isomerization zone; and
    (l2) contacting the para-xylene depleted stream with a first catalyst in the ethylbenzene removal zone under conditions effective to remove at least part of the ethylbenzene in the para-xylene depleted stream prior to (e2).

8. The process of claim 6, wherein the conditions in the ethylbenzene removal zone are effective to maintain the para-xylene depleted stream substantially in the gas phase.

9. The process of claim 7, wherein the conditions in the xylene isomerization zone are effective to maintain the para-xylene depleted stream substantially in the liquid phase.

10. The process of claim 1 and further comprising:
    (m2) removing a $C_{8+}$ hydrocarbon residue stream from the further dividing wall distillation column; and
    (n2) supplying at least part of the $C_{8+}$ hydrocarbon residue stream to the para-xylene recovery unit.

* * * * *